United States Patent
Huh et al.

(10) Patent No.: US 12,059,376 B2
(45) Date of Patent: Aug. 13, 2024

(54) PROTECTOR FOR WELDING

(71) Applicant: OTOS WING.CO., LTD., Seoul (KR)

(72) Inventors: Moon Young Huh, Seoul (KR); Sung Won Huh, Seoul (KR)

(73) Assignee: OTOS WING.CO., LTD., Geumcheon-gu (KR)

( * ) Notice: Subject to any disclaimer, the term of this patent is extended or adjusted under 35 U.S.C. 154(b) by 293 days.

(21) Appl. No.: 17/324,572

(22) Filed: May 19, 2021

(65) Prior Publication Data

US 2021/0378868 A1    Dec. 9, 2021

(30) Foreign Application Priority Data

Jun. 3, 2020 (KR) .................. 10-2020-0067174

(51) Int. Cl.
*A61F 9/06* (2006.01)

(52) U.S. Cl.
CPC .................... *A61F 9/06* (2013.01)

(58) Field of Classification Search
CPC ..... A61F 9/06; Y10S 2/11; A42B 3/14; A42B 3/142; A42B 3/147
USPC ............................................. 2/8.2
See application file for complete search history.

(56) References Cited

U.S. PATENT DOCUMENTS

| | | | | |
|---|---|---|---|---|
| 1,587,893 A | * | 6/1926 | Bowers | A61F 9/061 2/8.2 |
| 1,800,623 A | * | 4/1931 | Harlis | A61F 9/061 2/8.2 |
| 1,820,237 A | * | 8/1931 | Malcom | A61F 9/02 2/9 |
| 1,885,426 A | * | 11/1932 | Flood | A61F 9/06 2/8.2 |
| 2,358,978 A | * | 9/1944 | Huntsman | A61F 9/06 2/8.1 |
| 2,421,427 A | * | 6/1947 | Mamlin | A42B 3/225 2/5 |

(Continued)

FOREIGN PATENT DOCUMENTS

| | | |
|---|---|---|
| CN | 87212501 | 11/1988 |
| KR | 10-0894574 | 4/2009 |

(Continued)

OTHER PUBLICATIONS

Office Action for KR10-2020-0067174 submitted Oct. 26, 2021, all pages.

(Continued)

*Primary Examiner* — Grace Huang
(74) *Attorney, Agent, or Firm* — Kilpatrick Townsend & Stockton LLP

(57) ABSTRACT

According to an embodiment of the present disclosure, provided is a welding protector including a head band including a band main body including a front support portion for supporting forehead of a user, a rear band portion arranged opposite to the band main body, and a support band portion connected to the front support portion and supporting an upper portion of the user's head, a face shield rotatably connected to the head band and protecting face of the user, and an auxiliary shield protecting a part of the user's head, wherein the auxiliary shield and the head band are connected to each other.

11 Claims, 17 Drawing Sheets

(56) References Cited

U.S. PATENT DOCUMENTS

| | | | | |
|---|---|---|---|---|
| 2,469,810 A * | 5/1949 | Bowers | ............ | A61F 9/06 |
| | | | | 2/8.1 |
| 2,798,222 A * | 7/1957 | Evans | ............ | A42B 3/225 |
| | | | | 2/9 |
| 2,986,396 A * | 5/1961 | Abbott | ............ | A63B 67/00 |
| | | | | 473/502 |
| 3,026,523 A * | 3/1962 | Bowers, Sr. | ............ | A42B 3/14 |
| | | | | 2/416 |
| 3,475,766 A * | 11/1969 | Raschke | ............ | A42B 3/225 |
| | | | | 2/9 |
| 3,868,726 A * | 3/1975 | La Marre | ............ | A61F 9/06 |
| | | | | 2/8.1 |
| 4,117,554 A * | 10/1978 | Palumbo | ............ | A42B 3/225 |
| | | | | 2/418 |
| 4,766,609 A * | 8/1988 | Lane | ............ | A42B 3/225 |
| | | | | 2/5 |
| 4,790,032 A * | 12/1988 | Girouard | ............ | A41B 9/08 |
| | | | | 2/72 |
| 6,966,074 B2 * | 11/2005 | Huh | ............ | A42B 3/14 |
| | | | | 2/416 |
| 7,934,846 B1 * | 5/2011 | Schwanz | ............ | A61F 9/06 |
| | | | | 362/106 |
| 8,291,515 B2 * | 10/2012 | Carter | ............ | A41F 17/00 |
| | | | | 24/302 |
| 8,348,448 B2 * | 1/2013 | Orozco | ............ | A42B 1/244 |
| | | | | 2/182.2 |
| 8,611,075 B2 * | 12/2013 | Carter | ............ | A45F 5/02 |
| | | | | 361/679.01 |
| 8,875,318 B2 * | 11/2014 | Huh | ............ | A61B 90/35 |
| | | | | 2/416 |
| 9,066,552 B2 * | 6/2015 | Ahlgren | ............ | A42B 3/145 |
| 9,814,622 B2 * | 11/2017 | Sommers | ............ | A42B 3/225 |
| 10,441,019 B2 * | 10/2019 | Huh | ............ | A42B 3/12 |
| 11,058,586 B2 * | 7/2021 | Sommers | ............ | A42B 3/225 |
| 2015/0335093 A1 * | 11/2015 | Curci | ............ | A42B 3/225 |
| | | | | 2/424 |
| 2017/0238643 A1 * | 8/2017 | Pereira | ............ | A42B 3/14 |
| 2020/0205507 A1 * | 7/2020 | Sernfält | ............ | A61F 9/06 |
| 2020/0390182 A1 * | 12/2020 | Huh | ............ | A42B 3/142 |
| 2021/0076769 A1 * | 3/2021 | Kirshon | ............ | A42B 3/121 |
| 2021/0267804 A1 * | 9/2021 | Huh | ............ | A61F 9/06 |
| 2021/0361000 A1 * | 11/2021 | Choi | ............ | A41D 13/1184 |

FOREIGN PATENT DOCUMENTS

| | | |
|---|---|---|
| KR | 10-2011-0109156 | 10/2011 |
| KR | 10-2016-0146561 | 12/2016 |

OTHER PUBLICATIONS

Second Office Action for KR10-2020-0067174 submitted Jul. 27, 2022, all pages.

* cited by examiner

PROTECTOR FOR WELDING

CROSS-REFERENCE TO RELATED APPLICATIONS

This application is based on and claims priority under 35 U.S.C. § 119 to Korean Patent Application No. 10-2020-0067174, filed on Jun. 3, 2020, in the Korean Intellectual Property Office, the disclosure of which is incorporated by reference herein in its entirety.

TECHNICAL FIELD

One or more embodiments of the present invention relate to a protector for welding.

BACKGROUND ART

A welder wears a protector for protection from light and high temperature heat generated during a welding process such as arc welding. A protector has various shapes and structures such as a shape covering eyes of the welder or a shape covering head of the welder according to work of the welder.

DESCRIPTION OF EMBODIMENTS

Technical Problem

One or more embodiments of the present disclosure provide a protector for welding, having excellent assembling properties. However, the above technical features are exemplary, and the scope of the disclosure is not limited thereto.

Solution to Problem

According to an embodiment of the present disclosure, a welding protector includes: a head band including a band main body including a front support portion for supporting forehead of a user, a rear band portion arranged opposite to the band main body, and a support band portion connected to the front support portion and supporting an upper portion of the user's head; a face shield rotatably connected to the head band and protecting face of the user; and an auxiliary shield protecting a part of the user's head, wherein the auxiliary shield and the head band are connected to each other.

The auxiliary shield may include a pair of connection portions adjacent to both ears of the user, the support band portion or the connection portion may include a connection hole, and the auxiliary shield may include a protrusion connected to the connection hole.

The auxiliary shield and the head band may be connected through a detachable connection element interposed therebetween.

The connecting element may include a Velcro structure.

The auxiliary shield may include a cover portion including a fabric, and a pair of side portions disposed at opposite sides of the cover portion and including a material different from a material included in the cover portion.

An end portion in the auxiliary shield, which is adjacent to the face shield, may be curved toward the face shield.

An end portion of the auxiliary shield, which is adjacent to the face shield, may be located on an inner surface of a main body of the face shield.

Other aspects, features, and advantages other than the above-described features will be apparent from the following drawings, claims, and detailed descriptions of the disclosure.

Advantageous Effects

Embodiments of the present disclosure may provide a protector including an auxiliary shield, wherein the protector improves operation and wearing convenience, storage property, mobility, and the like. The above-described effects are exemplary, and the effects according to the embodiments will be described in detail below.

MODES OF DISCLOSURE

Figure 1:
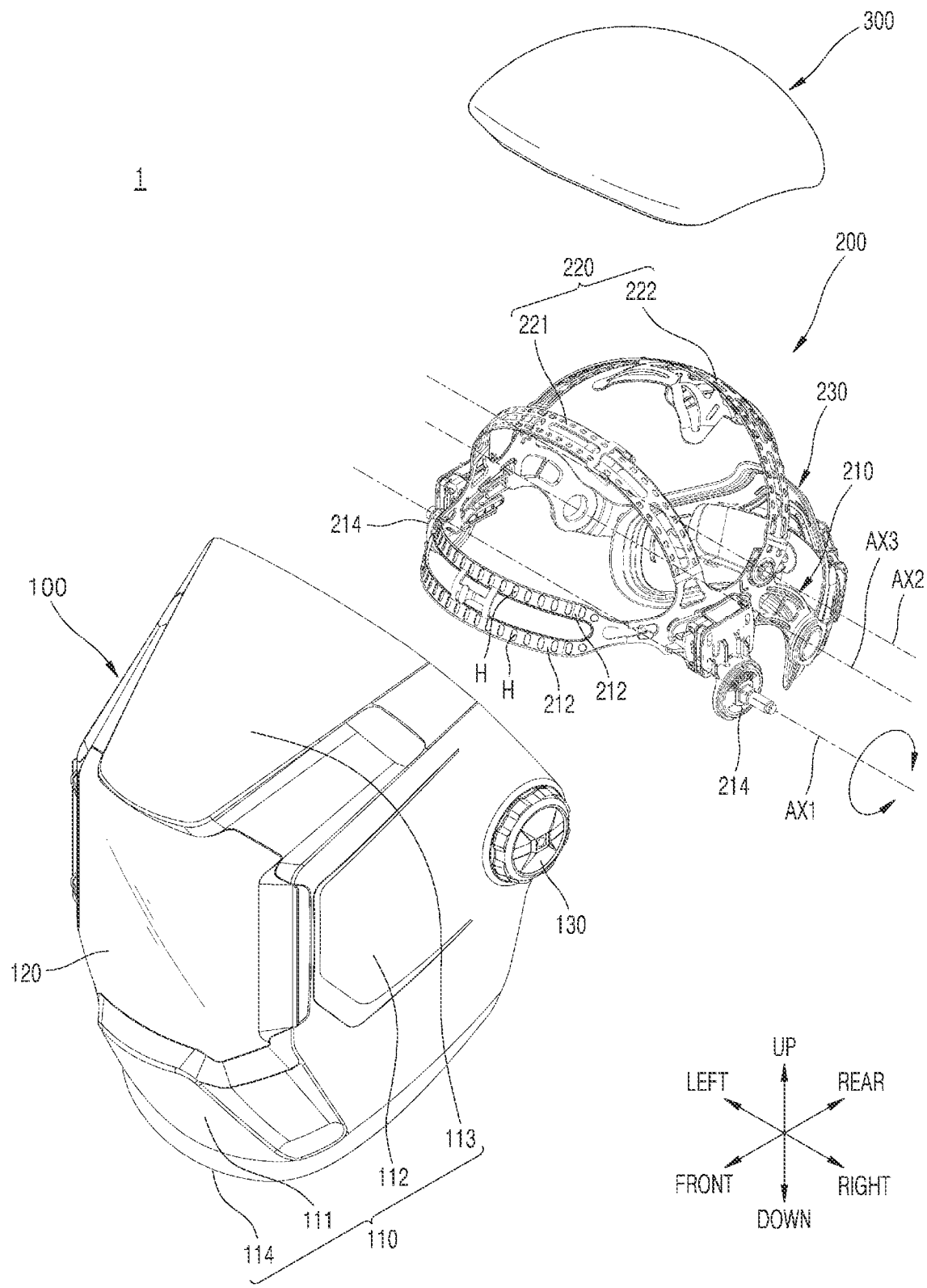
FIG. 1 is an exploded perspective view schematically illustrating a welding protector according to an embodiment of the present disclosure.

As the present disclosure allows for various changes and numerous embodiments, particular embodiments will be illustrated in the drawings and described in detail in the written description. The attached drawings for illustrating one or more embodiments are referred to in order to gain a sufficient understanding, the merits thereof, and the objectives accomplished by the implementation. However, the present disclosure is not limited to the embodiments described below, but may be implemented in various forms.

In the following embodiments, the terms "first" and "second" are not limited and are used to distinguish one component from other components.

In the following embodiments, an expression used in the singular encompasses the expression of the plural, unless it has a clearly different meaning in the context.

In the following embodiments, it is to be understood that the terms "including," "having," and "comprising" are intended to indicate the existence of the features or components disclosed in the specification, and are not intended to preclude the possibility that one or more other features or components may exist or may be added.

In the following embodiments, it will be understood that when a part such as a region, component, etc. is referred to as being "formed on" another portion, it may be directly or indirectly formed on the other portion, but intervening regions, or components may be present.

In the drawings, for convenience of description, the size of the elements may be exaggerated or reduced. For example, the size and thickness of each component shown in the drawings are arbitrarily shown for convenience of description, and thus the present disclosure is not limited thereto.

When a certain embodiment may be implemented differently, a specific process order may be performed differently from the described order. For example, two consecutively described processes may be performed substantially at the same time or performed in an order opposite to the described order.

In the following embodiments, when the area and the components are connected, the area and the components are directly connected to each other, and the other area and the components are indirectly connected to each other by being interposed therebetween.

Figure 2:
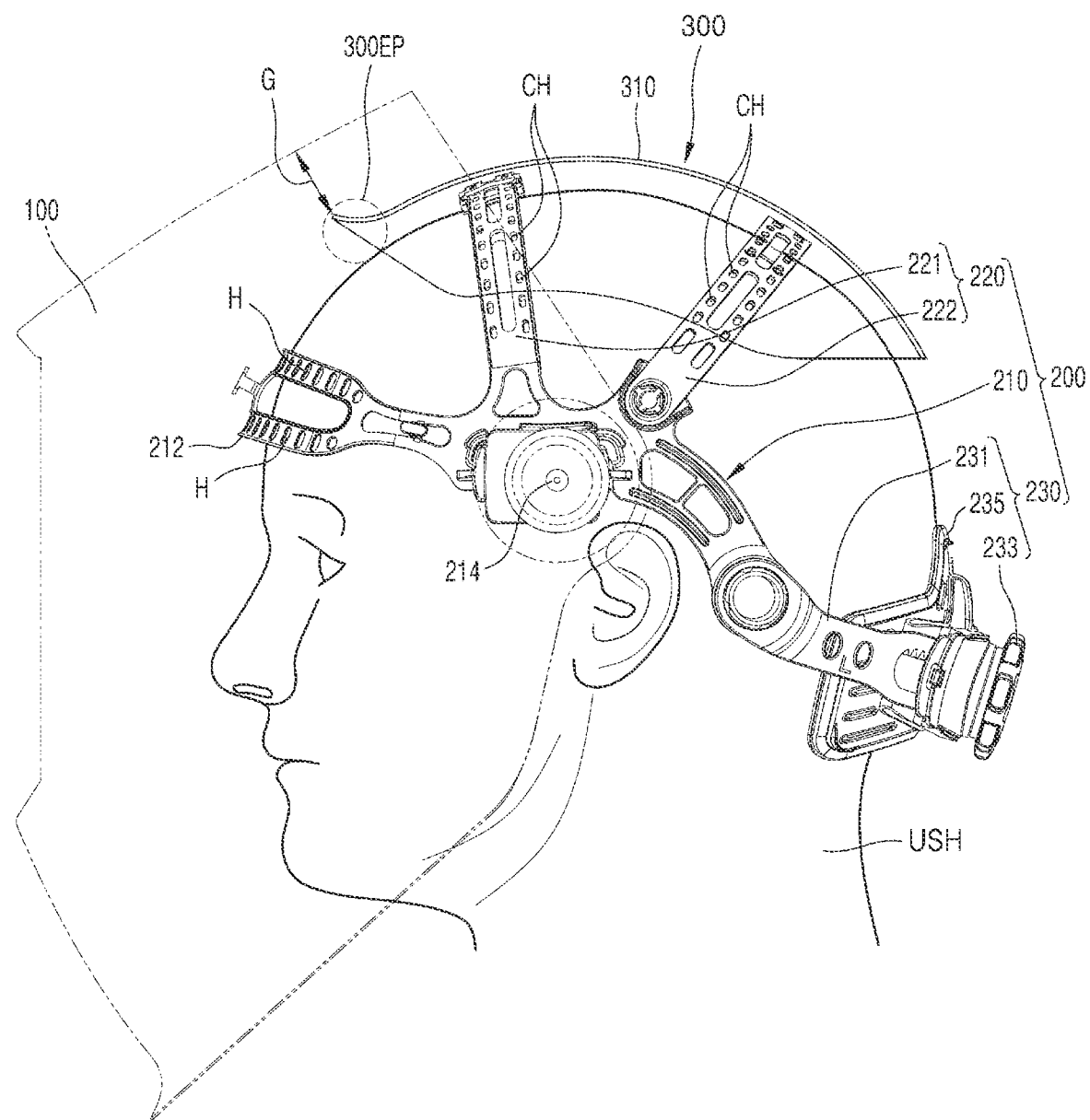
FIG. 2 is a side view schematically illustrating a state in which a welder wears a welding protector according to an embodiment of the present disclosure.

FIG. 1 is an exploded perspective view schematically illustrating a welding protector according to an embodiment of the present disclosure, and FIG. 2 is a side view schematically illustrating a state in which a welder wears the welding protector according to an embodiment of the present disclosure.

Referring to FIGS. 1 and 2, a welding protector 1 may include a face shield 100 protecting the face of a user USH, a head band 200 fixing the face shield 100 to the head of the user USH, and an auxiliary shield 300 covering another portion (e.g., a part of the head) of the body of the user USH that is not covered by the face shield 100.

The face shield 100 may protect the face of the user USH. The face shield 100 may include a body portion 110 and a darkening section 120 disposed at an area corresponding to eyes of the user USH.

The body portion 110 may include a hard material having a certain strength. The body portion 110 may include at least one of metal and plastic. In an embodiment, the body portion 110 may include a material that is resistant to elements such as spatters and sparks that may be generated during welding, and/or an external impact. For example, the body portion 110 may include heat-resistant plastic and/or reinforced plastic. The material included in the body portion 110 is distinguished from a material that does not maintain its own shape such as a fabric, and may maintain its own shape.

The body portion 110 may cover the face of the user USH including the eyes, nose, and/or mouth of the user USH. The body portion 110 may include a front surface portion 111 corresponding to the nose or/and mouth of the user USH, side surface portions 112 bent from the front surface portion 111 and disposed at left and right sides of the front surface portion 111, an upper surface portion 113 bent from the front surface portion 111 and disposed at an upper side of the front surface portion 111, and a lower surface portion 114 disposed opposite to the upper surface portion 113 and disposed adjacent to the jaw of the user USH.

The side surface portions 112, the upper surface portion 113, and the lower surface portion 114 may be bent from the front surface portion 111 at a certain angle and extend in a direction away from the front surface portion 111, and thus, the three-dimensional face of the user USH may be three-dimensionally protected by a main surface portion of the body portion 110.

The darkening section 120 may be exposed to outside through a part of the body portion 110, for example, an opening formed in the front surface portion 111, and may be disposed to correspond to the eyes of the user USH. The darkening section 120 may include a light-blocking filter. The light-blocking filter may include liquid crystal, and a darkening degree of the darkening section 120 may be adjusted according to an alignment direction of the liquid crystal. The darkening section 120 may include an automatic light-blocking filter. The automatic light-blocking filter may adjust the darkening degree based on light-sensing information of a sensor provided around the darkening section 120.

The head band 200 may connect the welding protector 1 to the head of the user USH. The head band 200 may include a band main body 210, a support band portion 220, and a rear band portion 230.

The band main body 210 is connected to the face shield 100, and may include a front support portion 212 that is in contact with or supports a front surface of the head of the user USH, for example, the forehead. The front support part 212 may be formed at a front side of the band main body 210. The front support portion 212 may include a plurality of holes H. Sweat from the head of the user USH is discharged or the skin of the user USH is exposed to air through the holes H during an operation such as welding or the like, to enable ventilation.

A pair of connection portions 214 may be disposed at opposite sides of the front support portion 212, for connection to the face shield 100. Pivot portions 130 disposed on opposite sides of the body portion 110 of the face shield 100 may be connected to the connection portions 214 of the head band 200, and thus, the face shield 100 may rotate at a certain angle about a first axis AX1 that passes through a connecting axis of the connection portions 214 and the pivot portions 130 connected to each other. The face shield 100 may cover the face of the user USH during the welding operation of the user USH and may not cover the face of the user USH by rotating about the first axis AX1 while being connected to the head band 200 when the welding operation is not performed.

Although FIG. 1 illustrates that the front support portion 212 is formed in two band strip type, in another embodiment, the front support portion 212 may have a one band strip type, a structure in which three or more band strips are arranged in parallel, or a structure in which two or more band strips cross each other like an X shape.

The support band portion 220 may be in contact with an upper portion of the head of the user USH or may support the upper portion of the head. The support band portion 220 may include at least one, for example, as illustrated in FIGS. 1 and 2, a plurality of sub-support band portions 221 and 222, for example, two sub-support band portions 221 and 222. Between the two sub-support band portions 221 and 222, the first sub-support band portion 221 may be disposed on the front portion relatively adjacent to the forehead of the user USH, and the second sub-support band portion 222 may be disposed on a parietal region to be relatively adjacent to an occipital region of the user USH. An angle between the first sub-support band portion 221 and the second sub-support band portion 222 may be less than 180°. In more detail, an angle between the first sub-support band portion 221 and the second sub-support band portion 222 may be less than about 90°.

The first sub-support band portion 221 may be integrally formed with the band main body 210, and the second sub-support band portion 222 may be rotatably connected to the band main body 210. For example, the second sub-support band portion 222 may be connected to the band main body 210 to be rotatable about the second axis AX2. The second axis AX2 may pass through a connection portion between the second sub-support band portion 222 and the band main body 210, that is, an overlapping portion therebetween.

Each of the first and second sub-support band portions 221 and 222 may include connection holes CH. The connection holes CH may allow sweat generated from the head of the user USH to be discharged or may enable ventilation. In addition, the connection holes CH may include a structure for connecting with the auxiliary shield 300.

The rear band portion 230 may be positioned opposite to the band main body 210 and may be rotatably connected to the band main body 210. For example, the rear band portion 230 may be connected to the band main body 210 to be rotatable about a third axis AX3. The rear band portion 230 may have a structure that supports or contacts the occipital region of the user USH and may have an adjustable length.

Each of the second axis AX2 and the third axis AX3 may be disposed at a position that is different from the first axis AX1. For example, the first axis AX1 may be disposed around the temple of the user USH, the second axis AX2 may be disposed on a line extending from the user's ear to the top of the head of the user USH, and the third axis AX3 may be disposed on a line extending from behind the user's ear to the occipital region.

The band main body 210, the support band portion 220, and the rear band portion 230 of the head band 200 may include the same material, or at least one selected from among the band main body 210, the support band portion 220, and the rear band portion 230 may include a material different from the others. The band main body 210, the support band portion 220, and the rear band portion 230 may include a plastic material.

The rear band portion 230 may include an adjusting band main body 231 connected to the band main body 210, a rear adjusting portion 233 connected to the adjusting band main body 231 for adjusting a length of the adjusting band main body 231, and a contact support portion 235 that is in direct contact with the occipital region of the user USH.

The rear adjusting portion 233 may include a rotatable lever, and may reduce or increase the length of the adjusting band main body 231 as the user USH rotates the lever in a clockwise or a counterclockwise direction.

The auxiliary shield 300 may cover an upper side of the head of the user USH. In this regard, FIG. 2 shows that the auxiliary shield 300 includes a cover portion 310 that covers the upper side of the head.

The auxiliary shield 300 may be connected to the head band 200. The auxiliary shield 300 may be detachably connected to the head band 200. In some embodiments, the head band 200 and the auxiliary shield 300 may be connected to each other via a structure including a connection hole CH and a protrusion, via a loop-and-fastener structure (e.g., a Velcro™ structure, or via a slide structure.

As shown in FIG. 2, the auxiliary shield 300 may cover the upper side of the head of the user USH, for example, a part of the parietal region thereof. A part of the auxiliary shield 300, e.g., a part of the auxiliary shield 300 adjacent to the forehead of the user USH, may overlap the face shield 100.

The auxiliary shield 300 may include one end portion 300EP that is curved or bent toward the face shield 100. In some embodiments, the end portion 300EP may also be curved toward the face shield 100. The one end portion 300EP of the auxiliary shield 300 may overlap the face shield 100, and a first gap G may be formed between the one end portion 300EP of the auxiliary shield 300 and the face shield 100 in a state in which the auxiliary shield 300 and the face shield 100 overlap each other. Alternatively, the one end portion 300EP of the auxiliary shield 300 may further extend than that illustrated in FIG. 2, and in this case, the first gap G may be about 3 mm or less, for example, 1 mm. Alternatively, the one end portion 300EP of the auxiliary shield 300 may be in direct contact with the inner surface of the face shield 100 (e.g., the first gap may be zero).

In some embodiments, the auxiliary shield 300 may have the same material as that of the face shield 100. For example, the auxiliary shield 300 may include a plastic material such as heat-resistant plastic and/or reinforced plastic.

In some embodiments, the auxiliary shield 300 may include a material that is different from that of the face shield 100. For example, the auxiliary shield 300 may include a resin material such as urethane or rubber, and/or a fabric.

Figure 3A:
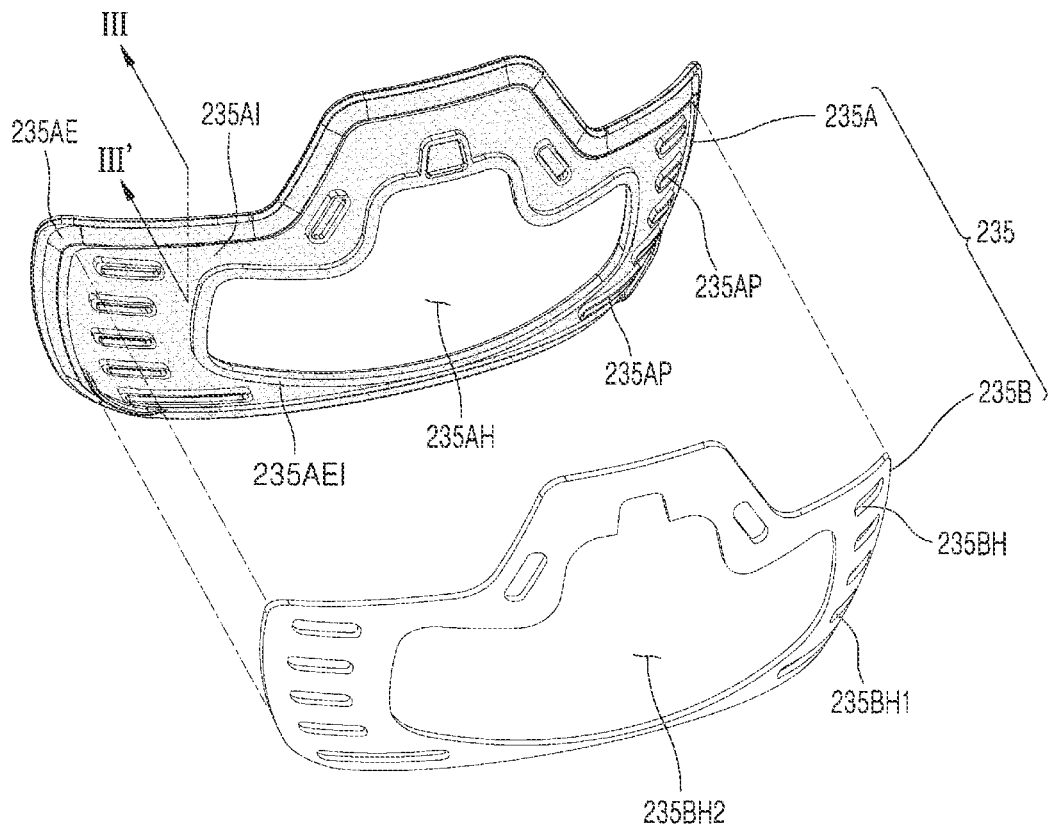
FIG. 3A is an exploded perspective view illustrating a rear band portion of a welding protector according to an embodiment of the present disclosure.
Figure 3B:
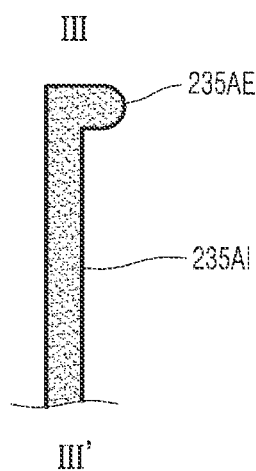
FIG. 3B is a cross-sectional view taken along line III-III' of FIG. 3A.
Figure 3C:
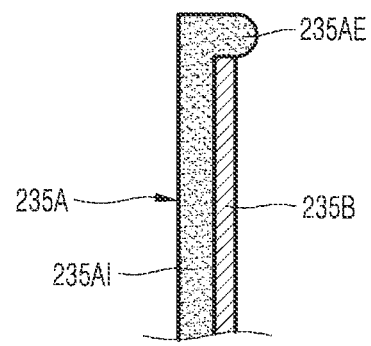
FIG. 3C is a cross-sectional view illustrating a connection state of a cushion pad and a support plate in a rear band portion according to an embodiment of the present disclosure.
Figure 3D:
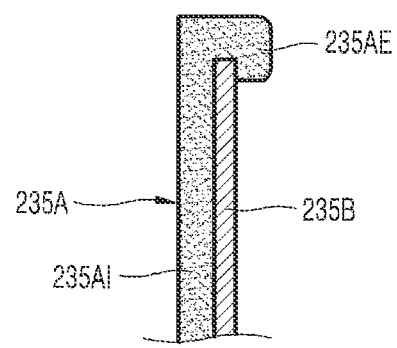
FIG. 3D is a cross-sectional view illustrating a connection state of a cushion pad and a support plate in a rear band portion according to another embodiment of the present disclosure.

FIG. 3A is an exploded perspective view illustrating a rear band portion of a welding protector according to an embodiment of the present disclosure, FIG. 3B is a cross-sectional view taken along line III-III' of FIG. 3A, FIG. 3C is a cross-sectional view illustrating a connection state between a cushion pad and a support plate of the rear band portion according to an embodiment of the present disclosure, and FIG. 3D is a cross-sectional view illustrating a connection state between a cushion pad and a support plate of a rear band portion according to another embodiment of the present disclosure.

As shown in FIG. 3A, the contact support portion 235 may include a cushion pad 235A and a support plate 235B connected to the cushion pad 235A. The cushion pad 235A may include a thermoplastic polyurethane (TPU) material.

One of the cushion pad 235A and the support plate 235B includes a protrusion and the other includes a hole, and the cushion pad 235A and the support plate 235B may be connected to each other through a connection structure between the protrusion and the hole. For example, the cushion pad 235A may include a plurality of protrusions 235AP, and the support plate 235B may include a plurality of first holes 235BH1 formed at positions corresponding to the plurality of protrusions 235AP.

An edge portion 235AE of the cushion pad 235A may form a step with respect to an inner portion 235AI disposed inside the edge portion 235AE. As shown in FIG. 3B, a thickness of the edge portion 235AE of the cushion pad 235A may be greater than a thickness of the inner portion 235AI. In some embodiments, as illustrated in FIG. 3C, the support plate 235B may be in direct contact with the inner portion 235AI of the cushion pad 235A. An edge of the support plate 235B may be in direct contact with the edge portion 235AE of the cushion pad 235A.

Each of the cushion pad 235A and the support plate 235B may include a hole formed in a center portion thereof. For example, the support plate 235B may include a second hole 235BH2, and the cushion pad 235A may include a hole 235AH (hereinafter, referred to as a third hole) overlapping the second hole 235BH2. The cushion pad 235A may include an inner edge portion 235AEI surrounding the third hole 235AH, and the inner edge portion 235AEI may form a step with respect to the inner portion 235AI like the edge portion 235AE.

FIGS. 3B and 3C illustrate that the edge portion 235AE of the cushion pad 235A is bent once in a direction crossing a direction in which the inner portion 235AI extends, and has an approximately L-shape. In another embodiment, the edge portion 235AE of the cushion pad 235A may be bent once in the direction crossing the direction in which the inner portion 235AI extends, and then is bent once again in a direction parallel to the direction in which the inner portion 235AI extends. Thus, the edge portion 235AE may have an approximately U-shape as shown in FIG. 3D. Referring to FIG. 3D, the edge of the support plate 235B may be inserted between the inner portion 235AI and the edge portion 235AE of the cushion pad 235A. For example, the edge of the support plate 235B may be inserted into a gap between the inner portion 235AI and the edge portion 235AE of the cushion pad 235A.

Figure 3E:
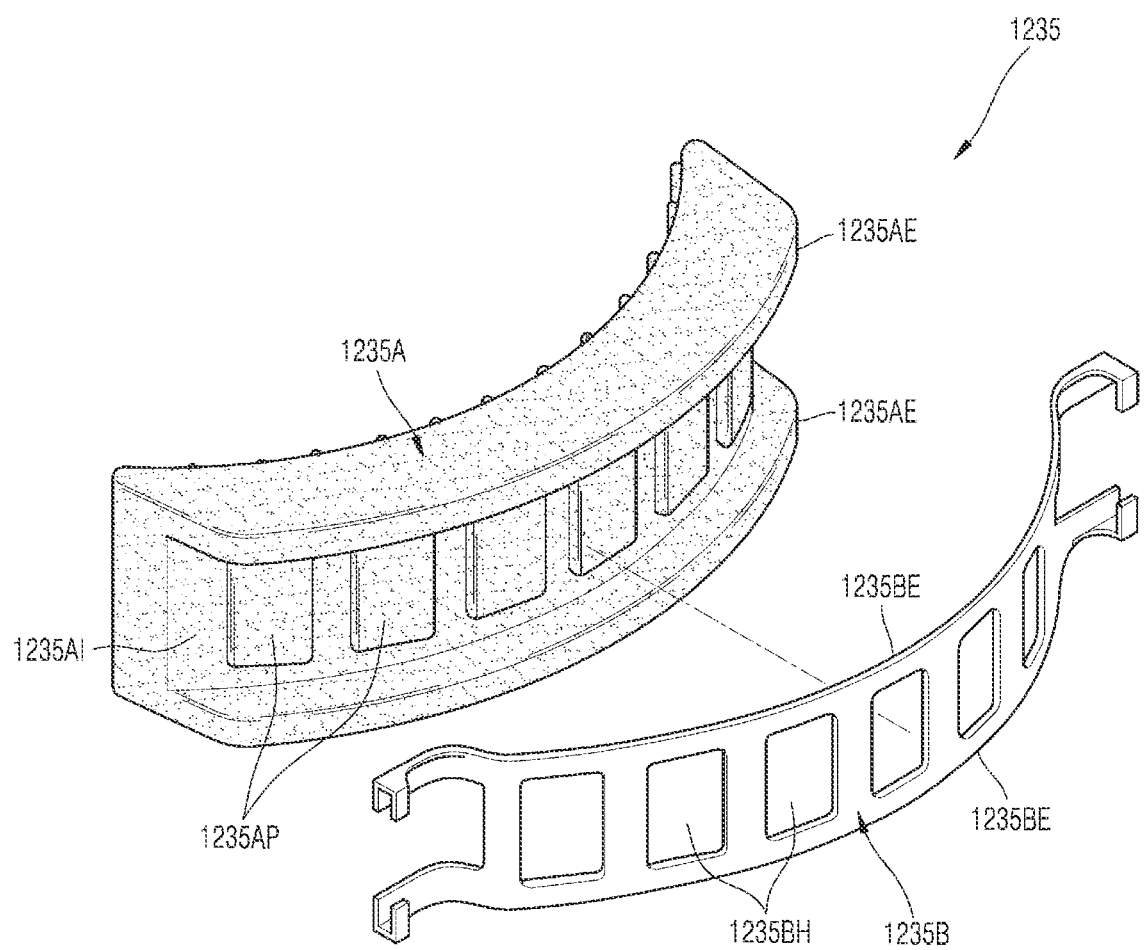
FIG. 3E is an exploded perspective view schematically illustrating a contact support portion according to another embodiment of the present disclosure.

FIG. 3E is an exploded perspective view schematically illustrating a contact support portion according to another embodiment of the present disclosure.

Referring to FIG. 3E, a contact support portion 1235 may include a cushion pad 1235A and a support plate 1235B connected to the cushion pad 1235A as shown in FIG. 3E. The cushion pad 1235A may include a TPU material.

One of the cushion pad 1235A and the support plate 1235B may include a protrusion and the other may include a hole, and the cushion pad 1235A and the support plate 1235B may be connected to each other through a connection structure between the protrusion and the hole. For example, the cushion pad 1235A may include a plurality of protrusions 1235AP, and the support plate 1235B may include a plurality of first holes 1235BH1 formed at positions corresponding to the plurality of protrusions 1235AP.

An edge portion 1235AE of the cushion pad 1235A may form a step with an inner portion 1235AI disposed inside the edge portion 1235AE. As illustrated in FIG. 3E, a thickness of the edge portion 1235AE of the cushion pad 1235A may be greater than a thickness of the inner portion 1235AI, and the support plate 1235B may be in direct contact with the inner portion 1235AI of the cushion pad 1235A. An edge 1235BE of the support plate 1235B may be in direct contact with the inside of the edge portion 1235AE of the cushion pad 1235A.

Figure 3F:
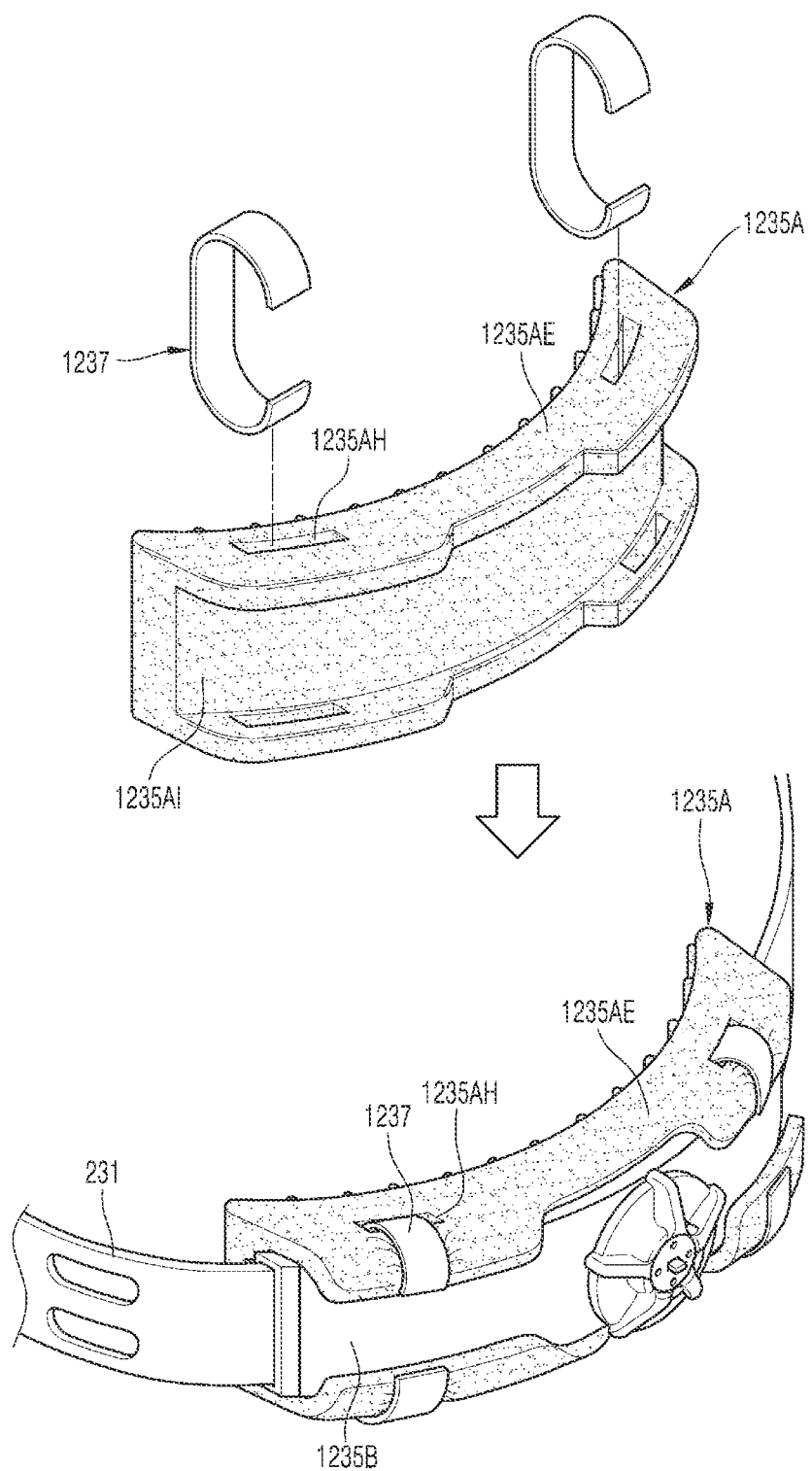
FIG. 3F is an exploded perspective view schematically illustrating a contact support portion according to another embodiment of the present invention.

FIG. 3F is an exploded perspective view schematically illustrating a contact support portion according to another embodiment of the present disclosure.

Referring to FIG. 3F, the cushion pad 1235A may include holes 1235AH formed in the edge portion 1235AE. The cushion pad 1235A may include the inner portion 1235AI, and a pair of edge portions 1235AE located on a virtual plane different from that of the inner portion 1235AI and located at opposite sides of the inner portion 1235AI. The holes 1235AH formed respectively in the pair of edge portions 1235AE may be disposed to face each other.

A clip 1237 may have an approximately C-shape and may have predetermined elasticity. The clip 1237 may include a polymer resin such as plastic. The clip 1237 may be inserted into the holes 1235AH formed in the pair of edge portions 1235AE facing each other, and as shown in FIG. 3F, the clip 1237 may couple the cushion pad 1235A and the support plate 1235B to each other. The support plate 1235B may be disposed to face the inner portion 1235AI of the cushion pad 1235A, and a center portion of the clip 1237 may be positioned between the inner portion 1235AI of the cushion pad 1235A and the support plate 1235B. In addition, opposite ends of the clip 1237 may be coupled to the cushion pad 1235A to apply a predetermined force to the corresponding edge portion 1235AE while passing through the holes 1235AH. The support plate 1235B may be a part of the adjusting band main body 231.

Although FIG. 3F illustrates that the clip 1237 is positioned on the inner portion 1235AI of the cushion pad 1235A, the present disclosure is not limited thereto. In another embodiment, as illustrated in FIG. 3G, the clip 1237 may be positioned on an outer portion 1235AO of the cushion pad 1235A.

Figure 3G:
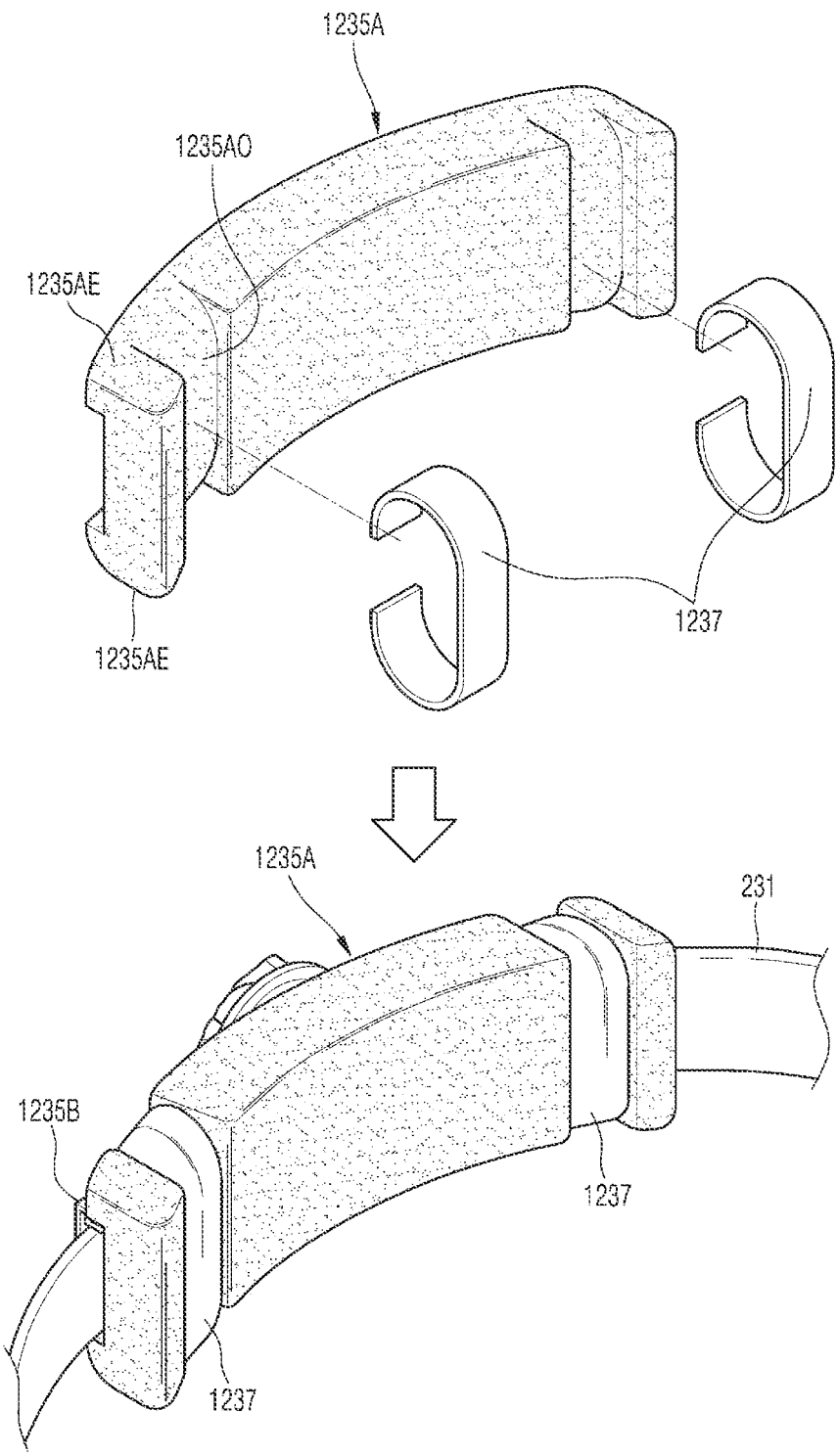
FIG. 3G is an exploded perspective view schematically illustrating a contact support portion according to another embodiment of the present invention.

FIG. 3G is an exploded perspective view schematically illustrating a contact support portion according to another embodiment of the present disclosure.

Referring to FIG. 3G, the clip 1237 may be placed on the outer portion 1235AO of the cushion pad 1235A. For example, a central portion of the clip 1237 may be in contact with the outer portion 1235AO of the cushion pad 1235A and opposite ends of the clip 1237 may each cover the edge portion 1235AE from the outside. In this case, as illustrated in FIG. 3G, a part of the cushion pad 1235A may be disposed between the center portion of the clip 1237 and the support plate 1235B. The cushion pad 1235A and the support plate 1235B may be connected by the clip 1237, as described above. In an embodiment, the support plate 1235B may be a part of the adjusting band main body 231.

Figure 4:
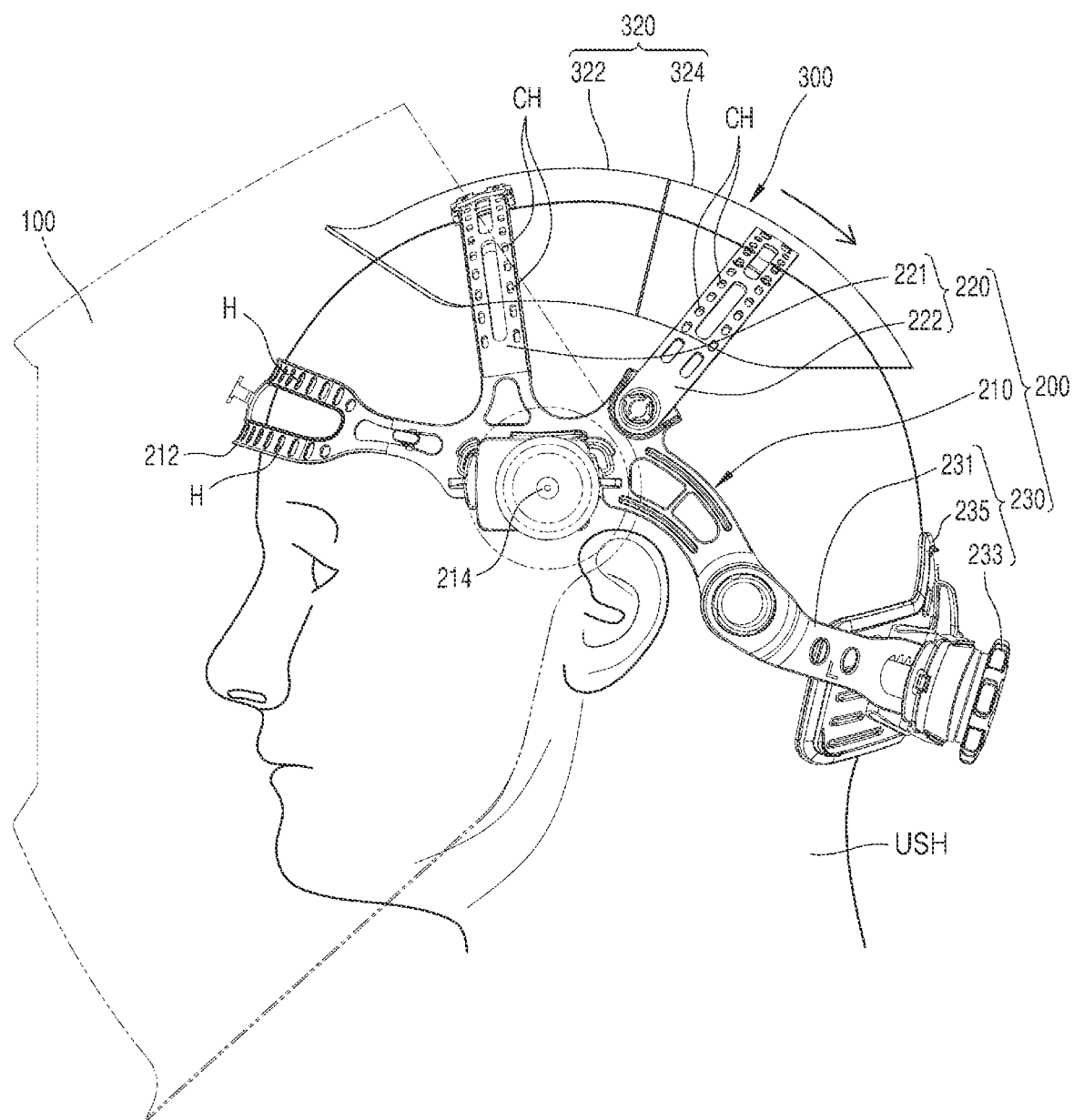
FIG. 4 is a side view schematically illustrating a state in which a user wears a welding protector according to an embodiment of the present disclosure.

FIG. 4 is a side view schematically illustrating a state in which a user wears the welding protector to an embodiment of the present disclosure.

Because the welding protector of FIG. 4 have the same characteristics as those of described above except for a detailed structure of the auxiliary shield 300, the welding protector will be described based on the auxiliary shield 300 hereinafter.

The auxiliary shield 300 may include a cover portion 320 covering an upper side of the head of the user USH, and the cover portion 320 may include a plurality of sub-shields. FIG. 4 shows that the auxiliary shield 300 includes two sub-shields, e.g., first and second sub-shields 322 and 324.

The first sub-shield 322 may cover an upper side, e.g., parietal region, of the head relatively close to the forehead of the user USH, and the second sub-shield 324 may be disposed farther from the forehead of the user USH than the first sub-shield 322.

The first sub-shield 322 may be connected to the first sub-support band portion 221. According to an embodiment, the first sub-shield 322 may include protrusions inserted into the connection holes CH of the first sub-support band portion 221 or may include an element including the above-described protrusions. According to an embodiment, the first sub-shield 322 may be connected to the first sub-support band portion 221 through a Velcro™ structure interposed therebetween, a hook structure, a clip structure, or a slide structure.

The second sub-shield 324 may be slidably connected to the first sub-shield 322. After the first sub-shield 322 is connected to the first sub-support band portion 221, the second sub-shield 324 may slide from the first sub-shield 322 in an arrow direction illustrated in FIG. 4. After that, the second sub-shield 324 may be connected to the connection holes CH of the second sub-support band portion 222. For example, the second sub-shield 324 may include protrusions inserted into the connection holes CH of the second sub-support band portion 222. Alternatively, the second sub-shield 324 may be connected to the second sub-support band portion 222 through a Velcro™ structure interposed therebetween, a hook structure, a clip structure, or a slide structure.

The first and second sub-shields 322 and 324 may include the same material or different materials. The first and second sub-shields 322 and 324 may include a plastic material such as heat resistant plastic and/or reinforced plastic, a resin material such as urethane or rubber, and/or a fabric such as flame-retardant cloth.

Figure 5:
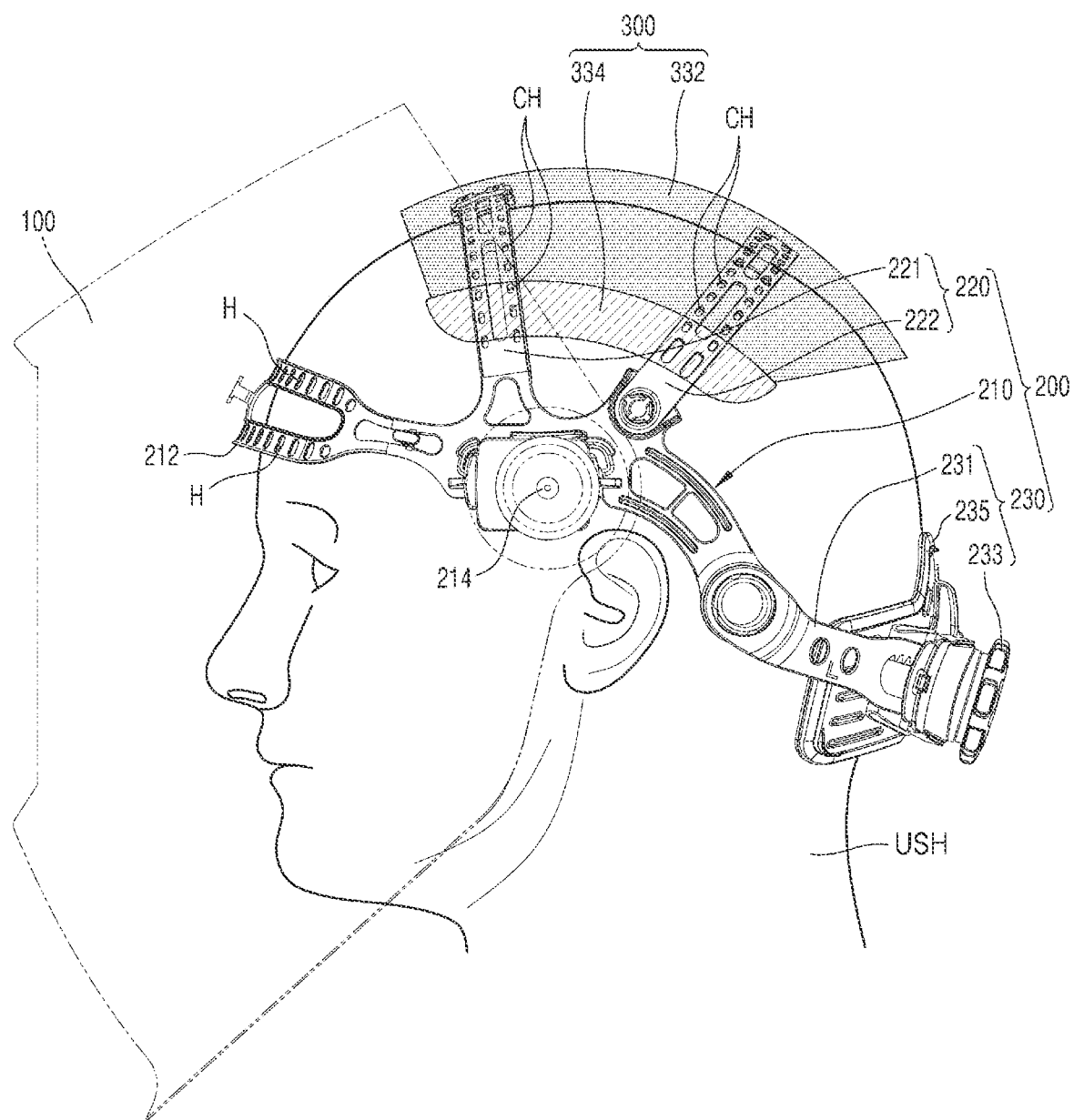
FIG. 5 is a side view schematically illustrating a state in which a user wears a welding protector according to an embodiment of the present disclosure.

FIG. 5 is a side view schematically illustrating a state in which a user wears the welding protector according to an embodiment of the present disclosure.

Because the welding protector of FIG. 5 have the same characteristics as those of described above except for a detailed structure of the auxiliary shield 300, the welding protector will be described based on the auxiliary shield 300 hereinafter.

The auxiliary shield 300 may include a cover portion 332 for covering the user's head and a pair of side portions 334 disposed at opposite sides of the cover portion 332. One of the pair of side portions 334 may be adjacent to the left ear of the user USH and the other may be adjacent to the right ear of the user USH.

The pair of side portions 334 may be connected to the support band portion 220. For example, the pair of side portions 334 may include protrusions inserted into the connection holes CH of the support band portion 220 or may further include an element including the above-described protrusions. Alternatively, the side portion 334 may be connected to the support band portion 220 through a Velcro™ structure interposed therebetween, a hook structure, a clip structure, or a slide structure.

The cover portion 332 may include a resin material such as urethane or rubber, and/or a fabric such as flame-retardant cloth. The pair of side portions 334 may include a plastic material such as heat-resistant plastic and/or reinforced plastic. When the cover portion 332 includes a material such as urethane, the pair of side portions 334 may partially overlap the cover portion 332.

Figure 6:
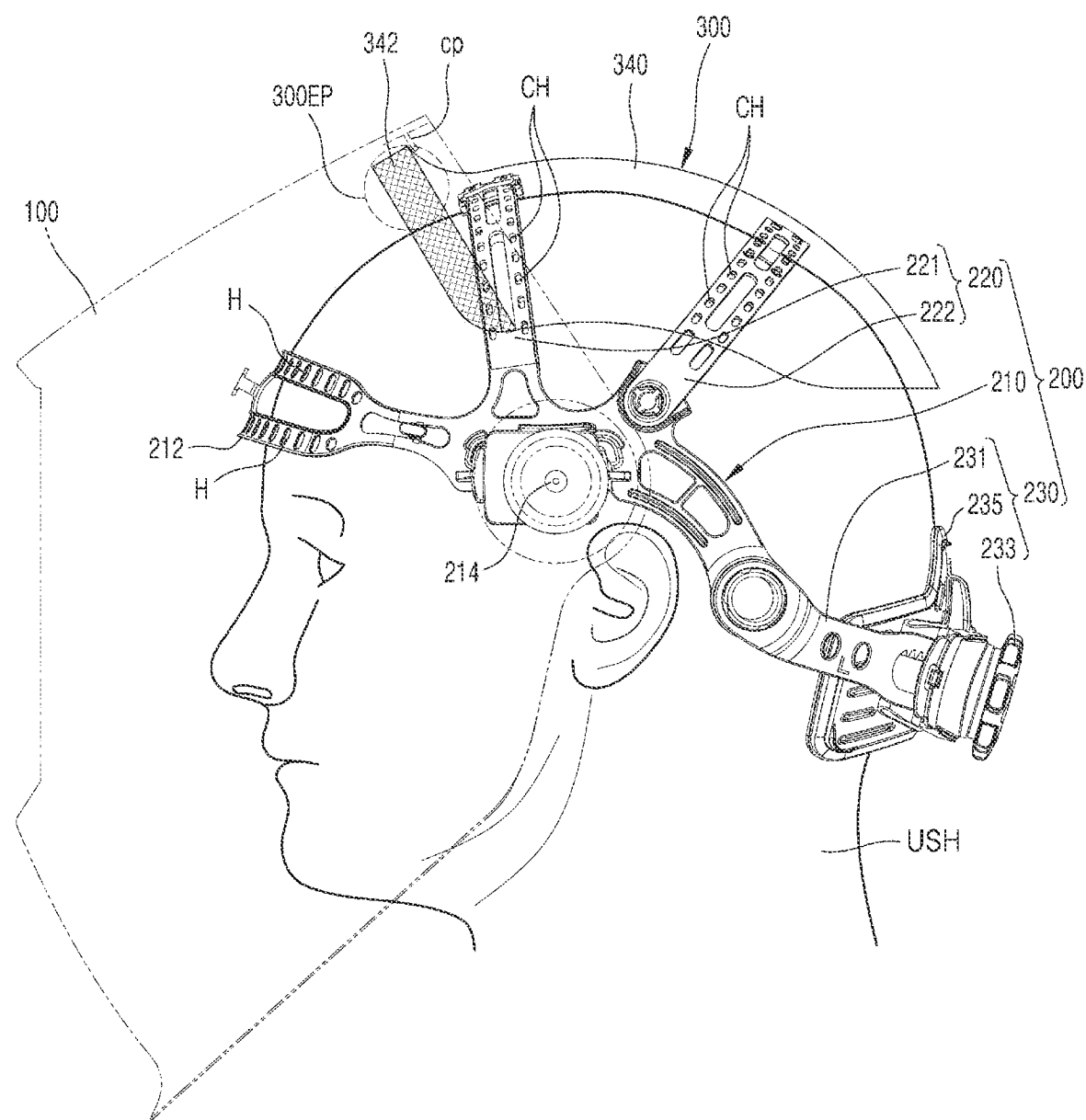
FIG. 6 is a side view schematically illustrating a state in which a user wears a welding protector according to an embodiment of the present disclosure.

FIG. 6 is a side view schematically illustrating a state in which a user wears the welding protector according to an embodiment of the present disclosure.

Because the welding protector of FIG. 6 have the same characteristics as those of described above except for a detailed structure of the auxiliary shield 300, the welding protector will be described based on the auxiliary shield 300 hereinafter.

Referring to FIG. 6, the auxiliary shield 300 may include a cover portion 340 that covers an upper side of the user's head. The cover portion 340 may include protrusions that may be inserted into the connection holes CH of the support band portion 220, or may further include an element including the above-described protrusions. Alternatively, the auxiliary shield 300 may be connected to the support band portion 220 through a Velcro™ structure interposed therebetween, a hook structure, a clip structure, or a slide structure.

One end portion of the cover portion 340 of the auxiliary shield 300 facing the forehead of the user USH, for example, one end portion 300EP facing the main body 110 may be located on an inner surface of the body portion 110.

In an embodiment, one end of the auxiliary shield 300, for example, one end portion 300EP of the cover unit 340, may include an edge surface 342 that faces the inner surface of the body portion 110 and has a predetermined width.

The edge surface 342 may be in direct contact with the inner surface of the body portion 110 or may be connected to the inner surface of the body portion 110 by using an adhesive layer, and thus there may be no gap between the cover portion 340 and the body portion 110. Therefore, light, spatter, and the like, which may be introduced through a gap between the cover portion 340 and the body portion 110, may be more effectively blocked.

In some embodiments, when the edge surface 342 is not connected to the inner surface of the body portion 110 by using an adhesive layer, or the like, a fine gap may exist between the end portion 300EP of the cover portion 340 and the inner surface of the body portion 110. The fine gap may overlap a cover protrusion CP protruding from the inner surface of the body portion 110. Therefore, light, spatter, and the like, which may be introduced through the fine gap described above, may be more effectively blocked.

In some embodiments, the edge surface 342 may be in direct contact with the inner surface of the body portion 110 or may be connected to the inner surface of the body portion 110 by using an adhesive layer, and the cover protrusion CP may be provided at the same time.

Figure 7:
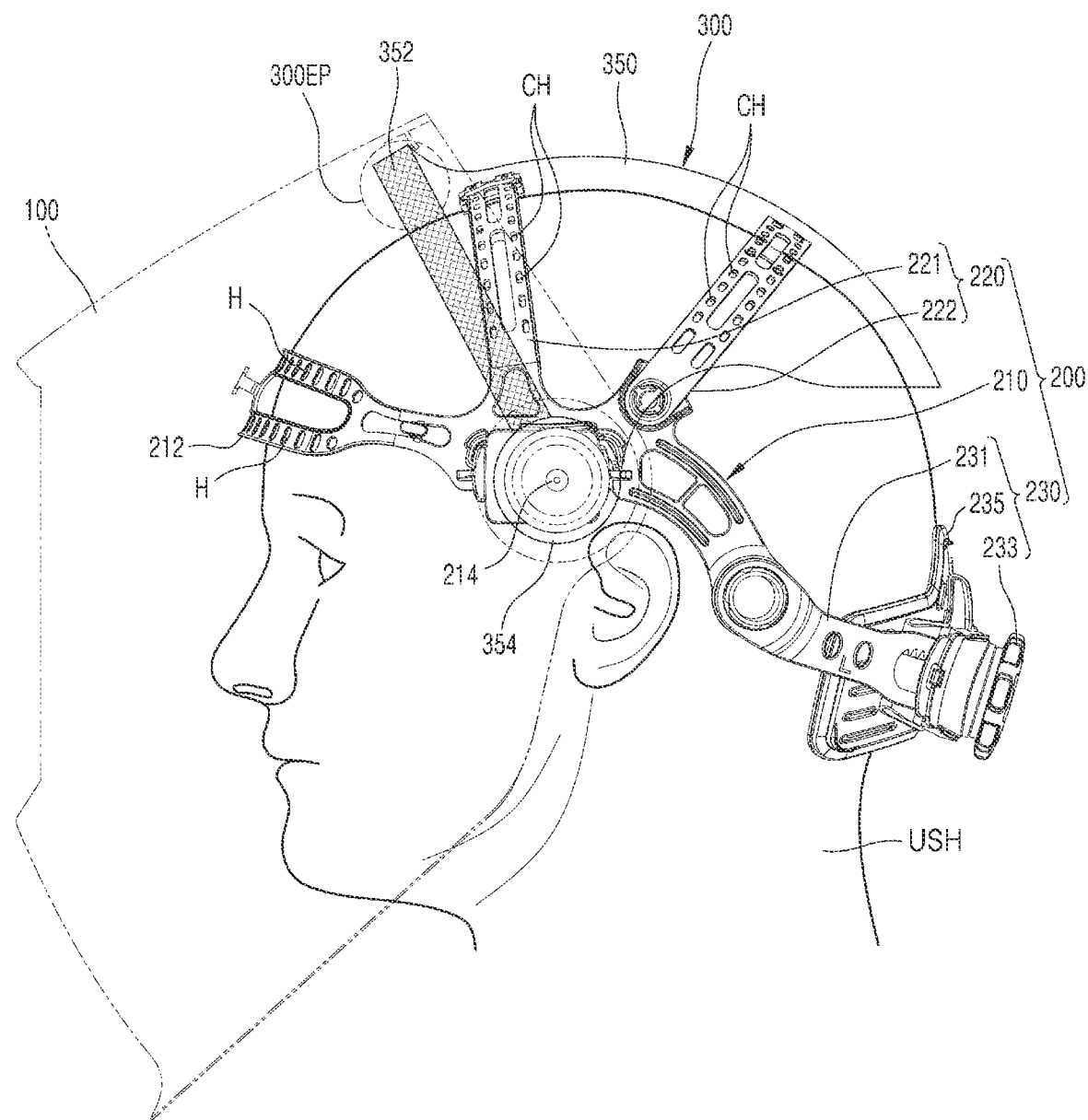
FIG. 7 is a side view schematically illustrating a state in which a user wears a welding protector according to an embodiment of the present disclosure.

FIG. 7 is a side view schematically illustrating a state in which a user wears the welding protector according to an exemplary embodiment of the present disclosure.

Because the welding protector of FIG. 7 have the same characteristics as those of described above except for a detailed structure of the auxiliary shield 300, the welding protector will be described based on the auxiliary shield 300 hereinafter.

Referring to FIG. 7, the auxiliary shield 300 may include a cover portion 350 for covering an upper side of the user's head, and one end portion 300EP of the cover portion 350 may be located on an inner surface of the body portion 110.

A relationship between the one end portion 300EP of the cover portion 350 and the body portion 110, for example, a structure in which the one end portion 300EP includes an edge surface 352 or the face shield 100 includes a cover protrusion, is the same as the above description with reference to FIG. 6.

The cover portion 350 may be connected to the support band portion 220 of the head band 200 and/or to the connection portions 214 of the head band 200. The cover portion 350 may include a pair of connection extension portions 354 each extending from a portion covering the head of the user toward each of the both ears of the user USH (or toward the connection portions 214 of the head band 200).

The pair of connection extension portions 354 may be respectively connected to the connection portions 214 of the head band 200, and the auxiliary shield 300 may rotate about an axis (e.g., the second axis AX2 of FIG. 1) passing through the pair of connection portions 214.

Figure 8:
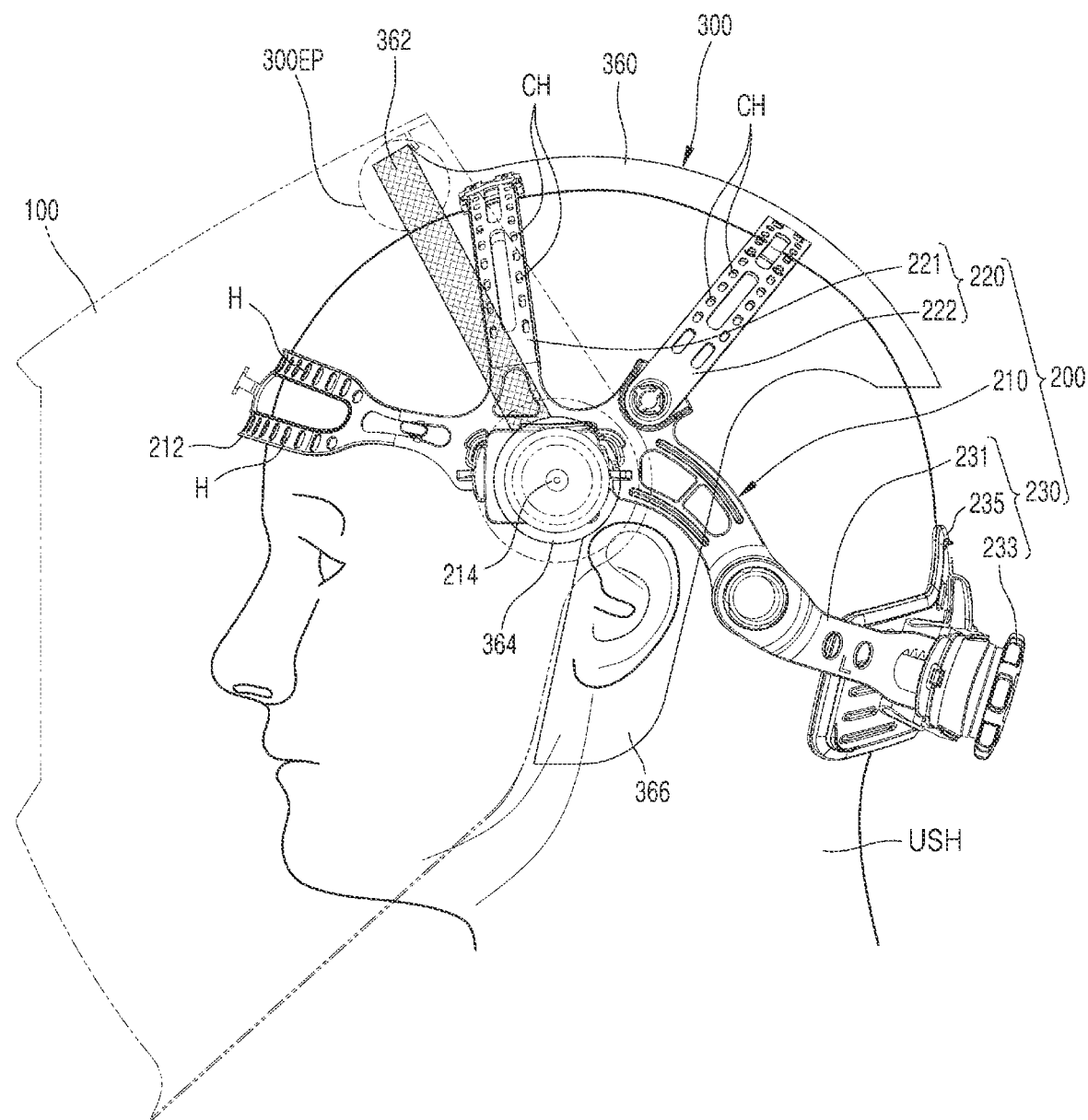
FIG. 8 is a side view schematically illustrating a state in which a user wears a welding protector according to an embodiment of the present disclosure.

FIG. 8 is a side view schematically illustrating a state in which a user wears the welding protector according to an embodiment of the present disclosure.

Because the welding protector of FIG. 8 have the same characteristics as those of described above except for a detailed structure of the auxiliary shield 300, the welding protector will be described based on the auxiliary shield 300 hereinafter.

Referring to FIG. 8, the auxiliary shield 300 may include a cover portion 360 for covering a user's head, and one end portion 300EP of the cover portion 360 may be located on an inner surface of the body portion 110. A relationship between the one end portion 300EP of the cover portion 360 and the body portion 110, for example, a structure in which the one end portion 300EP includes an edge surface 362 or the face shield 100 includes a cover protrusion, is the same as the above description with reference to FIGS. 6 and 7.

The cover portion 360 may be connected to the support band portion 220 of the head band 200 or may be connected to the connection portions 214 of the head band 200. The cover portion 360 may include a pair of connection extension portions 364 each extending from a portion covering the user's head toward each of the both ears of the user USH (or toward the connection portions 214 of the head band 200).

The pair of connection extension portions 364 may be respectively connected to the connection portions 214 of the head band 200, and the auxiliary shield 300 may rotate about an axis (e.g., the second axis AX2 of FIG. 1) passing through the pair of connection portions 214.

The cover portion 360 may include a pair of ear protection portions 366 respectively disposed adjacent to the pair of connection extension portions 364 and longer than the pair of connection extension portions 364. The ear protection portions 366 may be integrally formed with the cover portion 360 and may extend downward from the cover portion 360.

The auxiliary shield 300 described with reference to FIGS. 1, 2, and 4 to 8 may be connected to the support band portion 220 and/or the connection portions 214 of the head band 200, and a structure including protrusions and holes (or grooves) for connection therebetween will be described later with reference to FIGS. 9 to 14.

Figure 9:
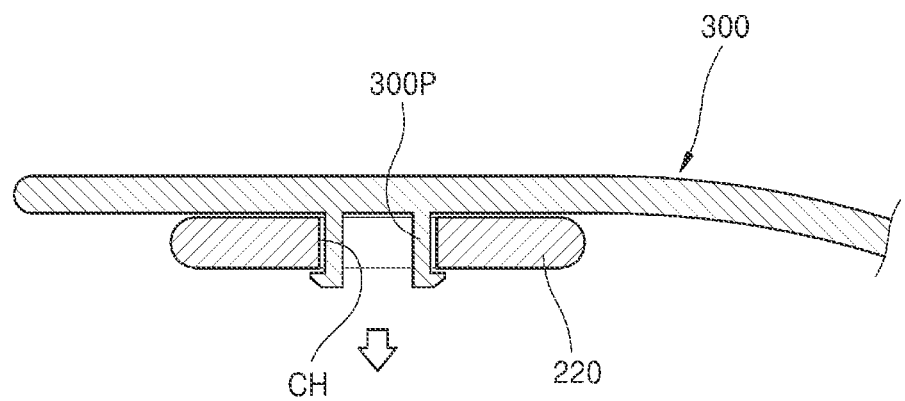
FIG. 9 is a cross-sectional view illustrating a connection between an auxiliary shield and a head band in a welding protector according to an embodiment of the present disclosure.

FIG. 9 is a cross-sectional view illustrating a connection between an auxiliary shield and a head band in a welding protector according to an embodiment of the present disclosure.

Referring to FIG. 9, the auxiliary shield 300 may include a protrusion 300P that may be connected to each connection hole CH formed in the support band portion 220 of the head band 200. The connection hole CH may be formed to pass through a second surface opposite to the first surface from the first surface of the support band portion 220, and the protrusion 300P may be inserted into the connection hole CH in a direction from the first surface toward the second surface of the support band portion 220.

In order to prevent the auxiliary shield 300 from being easily separated after being connected to the head band 200, an end portion of the protrusion 300P may be bent in an approximately L-shape.

Figure 10:
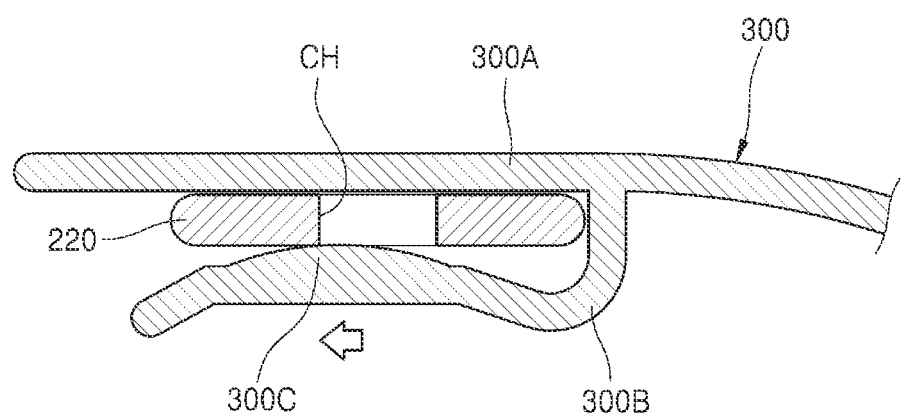
FIG. 10 is a cross-sectional view illustrating a connection between an auxiliary shield and a head band in a welding protector according to an embodiment of the present disclosure.

FIG. 10 is a cross-sectional view illustrating a connection between an auxiliary shield and a head band in a welding protector according to an exemplary embodiment of the present disclosure.

Referring to FIG. 10, the auxiliary shield 300 may include a protruding portion 300B protruding from a main surface portion 300A corresponding to a cover portion, and the protruding portion 300B may be bent to form a gap between the protruding portion 300B and the main surface portion 300A. The main surface portion 300A and the protruding portion 300B may have an approximately C-shape or U-shape.

The protruding portion 300B may include a protrusion 300C that overlaps the connection hole CH formed in the support band portion 220 of the head band 200 and is thicker than other portions. A gap between the protrusion 300C and the main surface portion 300A may be equal to or less than a thickness of the support band portion 220. The protrusion 300C may partially overlap the connection hole CH. In some embodiments, a part of the protrusion 300C may be accommodated in the connection hole CH.

Figure 11:
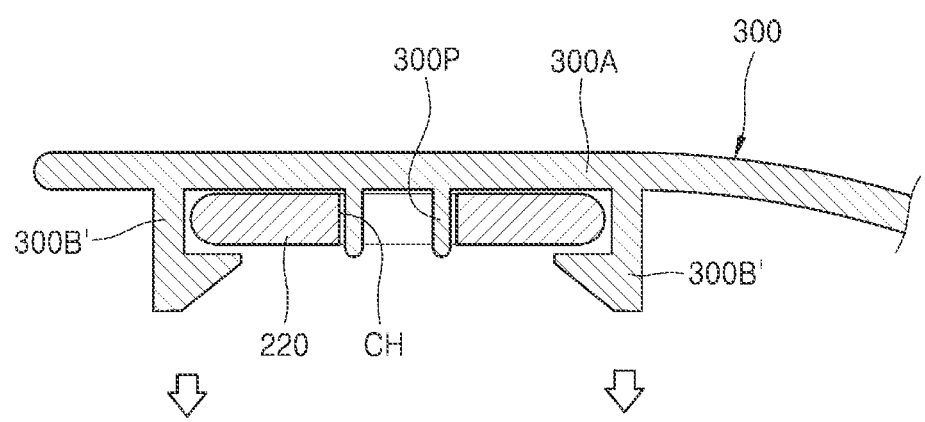
FIG. 11 is a cross-sectional view illustrating a connection between an auxiliary shield and a head band in a welding protector according to an embodiment of the present disclosure.

FIG. 11 is a cross-sectional view illustrating a connection between an auxiliary shield and a head band in a welding protector according to an embodiment of the present disclosure.

Referring to FIG. 11, the auxiliary shield 300 may include a pair of protruding portions 300B' protruding from the main surface portion 300A corresponding to the cover portion. A distance between the pair of protruding portions 300B' may correspond to a width of the support band portion 220, for example, a width of the first sub-support band portion or the second sub-support band portion described above with reference to FIG. 1.

The pair of protruding portions 300B' may be bent to form a gap between the pair of protrusion portions 300B' and the main surface portion 300A. Each of the pair of protruding portions 300B' extends from the main surface portion 300A of the auxiliary shield 300, and end portions of each of the pair of protruding portions 300B' may be bent toward each other. The auxiliary shield 300 may include protrusions 300P protruding from the main surface portion 300A.

The auxiliary shield 300 may move toward the support band portion 220, and at this time, the support band portion 220, for example, the first sub-support band portion or the second sub support band portion, may be located between a pair of protrusion portions 300B'. In this case, the protrusions 300P of the auxiliary shield 300 may be inserted into the connection hole CH of the support band portion 220 to fix a relative position between the auxiliary shield 300 and the support band portion 220. For example, connection between the protrusions 300P and the connection hole CH may prevent the support band portion 220 from sliding between the pair of protruding portions 300B'.

Figure 12A:
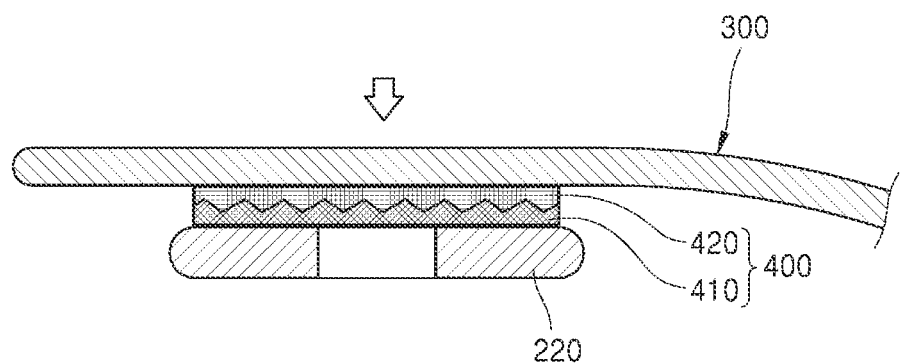
FIGS. 12A and 12B are cross-sectional views illustrating a connection between an auxiliary shield and a head band in a welding protector according to an embodiment of the present disclosure.
Figure 12B:
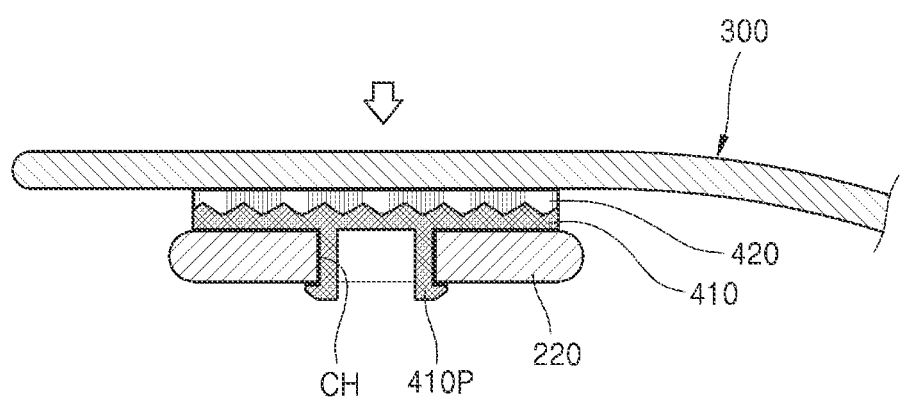

FIGS. 12A and 12B are cross-sectional views illustrating a connection between an auxiliary shield and a head band in a welding protector according to an embodiment of the present disclosure.

Referring to FIGS. 12A and 12B, a connecting assistant portion 400 may be arranged on a rear surface of the auxiliary shield 300 for connecting to the support band portion 220. The connecting assistant portion 400 may include a first portion 410 that is in direct contact with one of the auxiliary shield 300 and the support band portion 220 and a second portion 420 that is in direct contact with the other of the auxiliary shield 300 and the support band portion 220. The first portion 410 and the second portion 420 may be connected to each other via a Velcro™. In some embodiments, as shown in FIG. 12B, the first portion 410 may include a protrusion 410P for connecting to the connection hole CH of the support band portion 220.

Figure 13A:
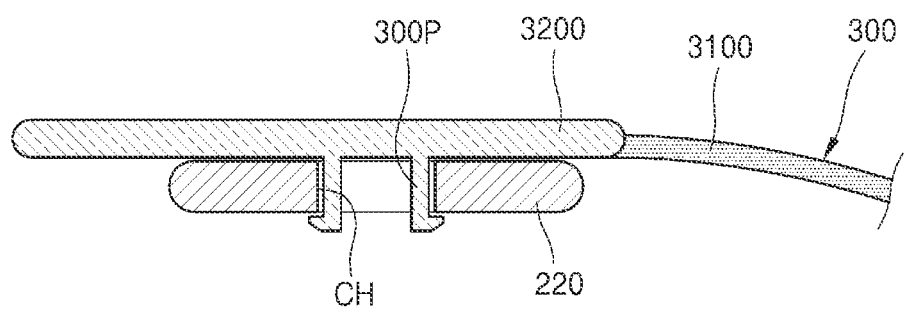
FIGS. 13A through 13C are cross-sectional views illustrating a connection between an auxiliary shield and a head band in a welding protector according to an embodiment of the present disclosure.
Figure 13B:
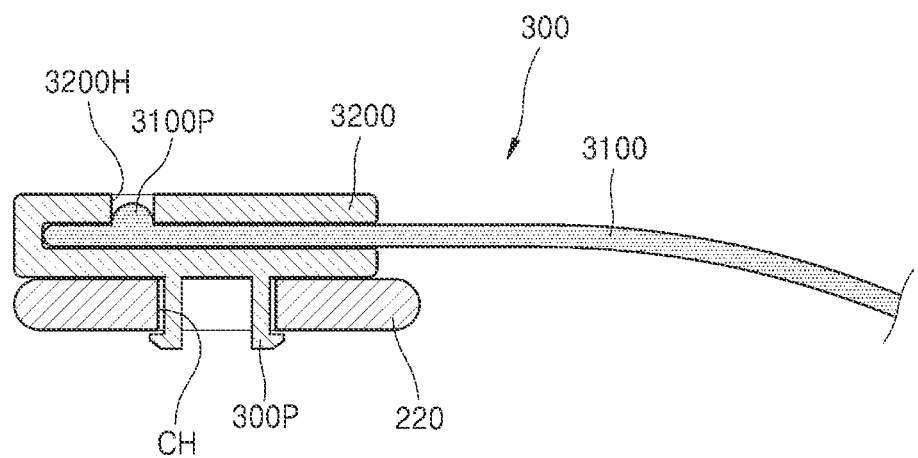
Figure 13C:
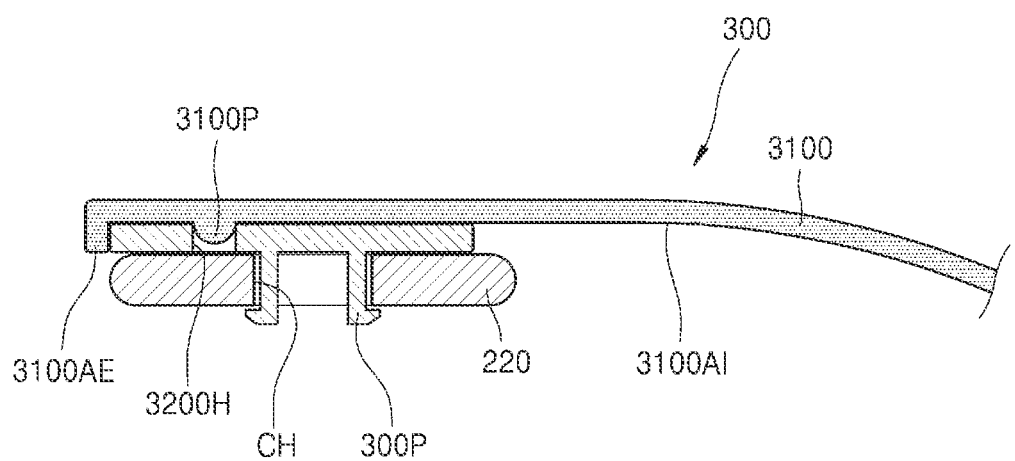

FIGS. 13A through 13C are cross-sectional views illustrating a connection between an auxiliary shield and a head band in a welding protector according to embodiments of the present disclosure.

Referring to FIGS. 13A to 13C, the auxiliary shield 300 may include a first material portion 3100 having a first material and corresponding to a cover portion, and a second material portion 3200 having a second material. In an embodiment, the first material portion 3100 and the second material portion 3200 may respectively correspond to the cover portion 332 and the side portion 334 described with reference to FIG. 5.

As illustrated in FIGS. 13A to 13C, the second material portion 3200 of the auxiliary shield 300 may include the protrusion 300P that may be connected to the connection hole CH of the support band portion 220.

The second material portion 3200 may be formed by a hetero-injection molding process when the first material portion 3100 is formed, as illustrated in FIG. 13A. In some embodiments, the second material portion 3200 may include a plastic material, and the first material portion 3100 may include a fabric such as flame-retardant cloth.

In some embodiments, when the first material portion 3100 includes a resin material such as urethane, the second material portion 3200 may be located on the upper surface of the first material portion 3100 as illustrated in FIG. 13B. The first material portion 3100 may include a protrusion 3100P, and the second material portion 3200 may include a hole 3200H in which the protrusion 3100P is accommodated. The second material portion 3200 may be bent to have an approximately C-shape, and the first material portion 3100 may be located between the bent portions of the second material portion 3200.

According to another embodiment, referring to FIG. 13C, the second material portion 3200 may be located on a lower surface (e.g., a surface facing the user's head) of the first material portion 3100. The first material portion 3100 may include the protrusion 3100P, and the protrusion 3100P may protrude from the lower surface of the first material portion 3100.

An edge portion 3100AE of the first material portion 3100 may form a step with respect to an inner portion 3100AI. The second material portion 3200 may be located at a region, in the lower surface of the first material portion 3100, corresponding to the inner portion 3100AI, and an edge of the second material portion 3200 may be in direct contact with the edge portion 3100AE of the first material portion 3100.

Figure 14:
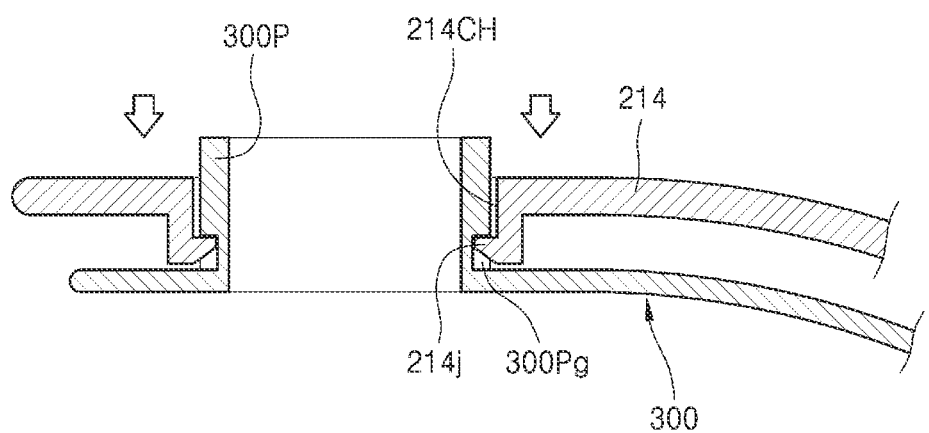
FIG. 14 is a cross-sectional view illustrating a connection between an auxiliary shield and a head band in a welding protector according to an embodiment of the present disclosure.

FIG. 14 is a cross-sectional view illustrating a connection between an auxiliary shield and a head band in a welding protector according to an embodiment of the present disclosure.

Referring to FIG. 14, the connection portions 214 of the head band may each include a connection hole 214CH. The auxiliary shield 300 may include the protrusion 300P that may be inserted into the connection hole 214CH.

A portion, in the connection portion 214, defining the connection hole 214CH may include an embossed portion 214j protruding toward an outer surface of the protrusion 300P, and the outer surface of the protrusion 300P may include a groove 300Pg for accommodating the embossed portion 214j.

The structure described with reference to FIG. 14 may correspond to the connection structure between the auxiliary shield 300 and the connection portion 214 described above with reference to FIGS. 7 and/or 8.

As described above, although the present disclosure has been described with reference to the embodiment illustrated in the drawings, it will be understood by those skilled in the art that various modifications and modifications of the embodiments are possible. Therefore, the scope sought to be protected of the disclosure shall be defined by the appended claims.

What is claimed is:

1. A welding protector comprising:
a head band including a band main body including a front support portion configured to support a forehead of a user's head, a rear band portion arranged opposite to the band main body, and a support band portion connected to the front support portion and configured to support an upper portion of the user's head;
a face shield rotatably connected to the head band and configured to protect a face of the user; and
an auxiliary shield configured to protect a part of the user's head,
wherein:
the support band portion defines a plurality of connection holes; and
the auxiliary shield includes a protrusion received in a connection hole of the plurality of connection holes.

2. The welding protector of claim 1, wherein
the auxiliary shield includes a pair of connection extension portions configured to be adjacent respectively to both ears of the user, and
the head band further includes a connection portion rotatably connected to one of the connection extension portions.

3. The welding protector of claim 1, wherein
the auxiliary shield and the head band are connected to each other via a connecting element that is attachable to/detachable from and interposed therebetween.

4. The welding protector of claim 3, wherein
the connecting element includes a loop structure.

5. The welding protector according to claim 1, wherein the auxiliary shield includes a cover portion including a fabric, and a pair of side portions disposed at opposite sides of the cover portion and including a material different from a material included in the cover portion.

6. The welding protector according to claim 1, wherein an end portion in the auxiliary shield, which is adjacent to the face shield, is curved toward the face shield.

7. The welding protector of claim 6, wherein the end portion is curved away from the head band toward the face shield.

8. The welding protector according to claim 1, wherein an end portion of the auxiliary shield, which is adjacent to the face shield, is configured to be located on an inner surface of a main body of the face shield.

9. The welding protector of claim 8, wherein the end portion is configured to be with the inner surface of the main body of the face shield.

10. The welding protector of claim 9, wherein:
the face shield includes a cover protrusion protruding from the inner surface of the main body; and
the end portion of the auxiliary shield configured to be in contact with the cover protrusion.

11. The welding protector of claim 1, wherein an end portion of the protrusion includes a major dimension greater than an opening dimension of the connection hole.

* * * * *